United States Patent [19]

Nelson

[11] 4,338,466
[45] Jul. 6, 1982

[54] PROSTAGLANDIN ANALOGS AND PROCESS OF PREPARATION THEREOF

[75] Inventor: George L. Nelson, Narberth, Pa.

[73] Assignee: The United States of America as represented by the Secretary of the Navy, Washington, D.C.

[21] Appl. No.: 250,366

[22] Filed: Apr. 2, 1981

[51] Int. Cl.$^3$ .................... C07C 49/597; C07C 45/45
[52] U.S. Cl. ................................... 568/343; 568/347; 568/348; 568/352; 568/379; 568/420
[58] Field of Search ............... 568/379, 343, 348, 347, 568/420, 352

[56] References Cited

U.S. PATENT DOCUMENTS

| | | | |
|---|---|---|---|
| 3,855,247 | 12/1974 | Fried | 568/379 |
| 3,981,891 | 9/1976 | Celli et al. | 568/379 |
| 4,039,563 | 8/1977 | Tanaka et al. | 568/379 |
| 4,053,341 | 11/1977 | Naipawer et al. | 568/379 |
| 4,073,799 | 2/1978 | Kondo et al. | 568/379 |
| 4,153,808 | 5/1979 | Polis et al. | 424/305 |
| 4,245,111 | 1/1981 | Polis et al. | 424/305 |

OTHER PUBLICATIONS

Fieser et al., "Reagents for Organic Synthesis", pp. 193 and 420 (1967).

*Primary Examiner*—Natalie Trousof
*Assistant Examiner*—James H. Reamer
*Attorney, Agent, or Firm*—R. S. Sciascia; Henry Hansen

[57] ABSTRACT

Prostaglandin analogs and process for the preparation thereof as precursors for the synthesis of oligomeric mixtures exhibiting biological activity for protection of oxidative phosphorylation of degraded mitochondria. The analogs have the general formula:

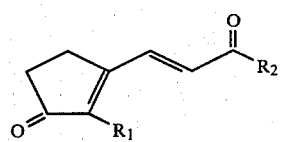

synthesized by O-alkylating a 2-alkylcyclopentane-1,3-dione to form an enol ether, reacting the ether with $CH_2=CHMgBr$ to form a vinyl, oxidizing the vinyl with $OsO_4$ and $NaIO_4$ to form an aldehyde, and reacting the aldehyde with a sodium salt of dimethyl (2-oxoalkyl)phosphonate.

10 Claims, No Drawings

PROSTAGLANDIN ANALOGS AND PROCESS OF PREPARATION THEREOF

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

The present invention relates to prostaglandin analogs, and process for the preparation thereof, as precursors for the synthesis of oligomeric mixtures showing biological activity with regard to the protection of oxidative phosphorylation in degenerated mitochondria. More particularly, the invention relates to such ethyl analogs and related compounds having low molecular weights and abbreviated side chains which make derived oligomers more amenable to structural elucidation by conventional techniques.

A new class of polymeric derivatives designated $PGB_x$ and the syntheses thereof are disclosed in U.S. Pat. No. 4,153,808 issued May 8, 1979 to B. David Polis et al., and U.S. Pat. No. 4,245,111 issued Jan. 13, 1981 to B. David Polis et al., which have the unique property of restoring the in vitro phosphorylating ability of degraded mitochondria. The precursors used in the syntheses are prostaglandins such as $PGB_1$, 13-14-dehydro-$PGB_1$ and 15-keto-$PGB_1$ methyl ester, each having a relatively complex molecular structure resulting in oligomeric derivatives which are not amenable to structural elucidation by conventional spectroscopic techniques necessary for defining the structure-activity relationships.

One well-known method of structural elucidation of the reaction products is by assignment of the carbon-13 chemical shifts. Unequivocal assignments are required in order that the precursors may serve as models for the components having the desired mitochondrial activity. However, the chemical shift assignments for the prior art precursors are based solely on analogy to other classes of prostaglandins not having disubstituted cyclopentenone systems. Thus, several assignments associated with the systems of $PGB_x$ were uncertain.

In addition, the prior methods of preparing the prostaglandin precursors of the oligomeric mixture $PGB_x$ are relatively inefficient and indirect, resulting in longer reaction times and higher costs.

SUMMARY OF THE INVENTION

Accordingly, it is an object of the present invention to provide new and novel precursors suitable for the rapid conversion to an oligomeric mixture, the physical and chemical characteristics of which protect mitochondria against the loss of oxidative phosphorylation. Another object of the invention is to provide prostaglandin analogs and related compounds, and process for preparation thereof, of the general formula:

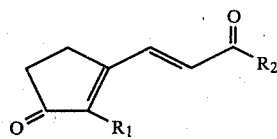

wherein $R_1$ and $R_2$ are alkyls including ethyl, methyl and n-pentyl. A further object is to provide precursors that will produce oligomeric mixtures more amenable to structural elucidation by spectroscopic techniques. Still another object is to provide precursors which are relatively inexpensive to produce and have significantly reduced preparation time.

Briefly, these and other objects of the invention are accomplished by new precursors, and method for preparing same, which will convert to oligomeric mixtures exhibiting the unique property of protection of the in vitro phosphorylating ability of degraded mitochondria. The new precursors, 3-(trans-3-keto-1-pentenyl)-2-ethyl-2-cyclopentenone and a series of closely related compounds, are synthesized by the following method: a 2-alkylcyclopentane-1,3-dione is O-alkylated to form an enol ether; the enol ether is reacted with vinyl magnesium bromide in ether to form a vinyl compound; the vinyl compound is oxidized with osmium tetraoxide and sodium periodate in aqueous ether to give an aldehyde; and the aldehyde is reacted with a sodium salt of dimethyl (2-oxoalkyl) phosphonate and the crude product is purified by chromatography to yield the new precursors.

For a better understanding of these and other objects and aspects of the invention, reference is made to the following detailed description.

DESCRIPTION OF THE PREFERRED EMBODIMENT

The general reaction formulas for the synthesis of the ethyl analogs and related compounds according to the invention and the specific examples illustrated infra are as follows:

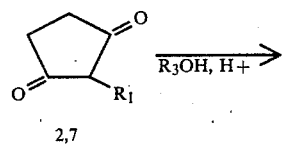
2,7

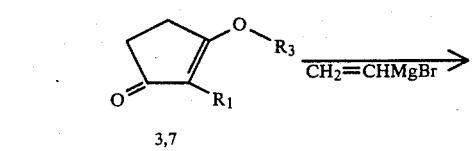
3,7

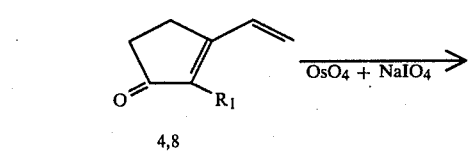
4,8

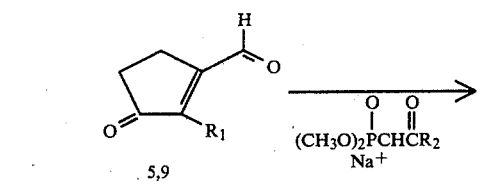
5,9

-continued

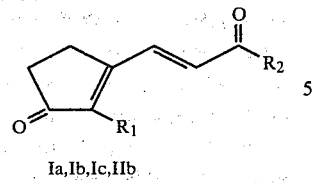

Ia,Ib,Ic,IIb

The branch radical $R_1$ is of the group consisting of ethyl (Et) and methyl (Me); and $R_2$ and $R_3$ are alkyls, such as Et, Me, and n-pentyl ($C_5H_{11}$). Precursors derived from reactants with their respective radicals are summarized in the following Table 1:

TABLE 1

| Precursor | $R_1$ | $R_2$ |
|-----------|-------|-------|
| Ia | Et | Et |
| Ib | Et | Me |
| Ic | Et | $C_5H_{11}$ |
| IIa | Me | Et |
| IIb | Me | Me |
| IIc | Me | $C_5H_{11}$ |

The following examples illustrate the process for the preparation of the new precursor according to the general formulas supra. Numbers associated with the compounds in the examples correspond to those shown in the general formulas. Parts stated are by weight, unless stated otherwise. Infrared (ir) spectra were recorded using a Perkin-Elmer Model 137 infrared spectrophotometer. Nuclear magnetic resonance (nmr) spectra were recorded on a Varian Model T-60 spectrometer operating at 60 MHz. Chemical shifts were measured in parts per million (ppm) downfield from tetramethylsilane (TMS), internal reference, on the δ-scale. The order of presentation of nmr data is as follows: chemical shift; multiplicity, s=singlet, d=doublet, t=triplet, q=quadruplet, m=multiple; integration; and assignment. Chromatography was performed on columns of silicic acid, 100–200 mesh. A mixed solvent of ethyl acetate-cyclohexane was used for elution.

PRECURSOR Ia

3-Methoxy-2-ethyl-2-cyclopentenone (3)

20 g of commercially available 2-ethyl-1,3-cyclopentanedione 2 partially dissolved in tetrahydrofuran (THF) was treated with etheral diazomethane generated from 50 g of N-methyl-N-nitroso-p-toluenesulfonamide, sold under the trademark Diazald (Aldrich Chemical Company). After standing several hours the solvent was removed under reduced pressure to give ca. 21 g of crude enol ether 3. Complete conversion to the enol ether 3 is obtained with a particularly clean reaction. But since the use of diazomethane is extremely hazardous, particularly when used in large scale reactions (greater than 20 grams), methanol with p-toluenesulfonic acid as the catalyst is preferred. The conversion to enol ether 3 is less complete, but the unreacted dione 2 can be recovered from the reaction mixture and recycled. The crude products of four reactions (84.1 g from 78.8 g of dione 2) were combined, dissolved in chloroform ($CHCl_3$) and extracted with 5% $NaHCO_3$. Removal of the $CHCl_3$ under reduced pressure gave 69.5 g of the enol ether 3 (79% from dione 2) which was free of unreacted dione 2 as indicated by an nmr analysis. Distillation under reduced pressure (bp 82°–84° at 0.03 nm) gave a light colored oil: uv max (95% ethanol) 253 nm; ir (neat) 1685 cm$^{-1}$ (cyclopentenone C=O) and 1620 cm$^{-1}$ (enolic double bond), 1360 and 1270 cm$^{-1}$ (enol ether); nmr ($CDCl_3$) δ4.0 (s, 3, —O$C\underline{H}_3$), 2.17 (q,2, —$C\underline{H}_2CH_3$ and 1.0 (t, 3, —$CH_2C\underline{H}_3$).

3-Vinyl-2-ethyl-2-cyclopentenone (4)

A three-necked, round-bottomed reaction flask equipped with a mechanical stirrer, reflux condenser, dropping funnel and nitrogen inlet is flamed out under nitrogen. After 65.6 g (0.5 mole) vinyl magnesium bromide in 500 ml THF was transferred to the flask, 35 g (0.25 mole) 3-methoxy-2-ethyl-2-cyclopentenone 3 in 100 ml of THF was then added over a period of 3 hours at room temperature. After stirring overnight at room temperature, the reaction mixture was poured onto 1 kg of cracked ice containing slightly less then the required amount of concentrated HCl. Additional concentrated HCl is added to bring the mixture to pH 3 and then the reaction mixture was extracted three times each with 150 ml $CHCl_3$. From the combined extract, chloroform ($CHCl_3$) was removed under reduced pressure to yield 40.6 g (119% of theoretical) of a crude, yellow vinyl compound 4. The crude products from several reactions were combined for purification by distillation. The compound 4 (114.6 g) was distilled (53°–54° C. at 0.1 mm) to yield 70.3 g (69%) of a light yellow oil: uv max (95% ethanol) 266 nm; ir (neat) 1690 cm$^{-1}$ (conj C=O)[1], 1630 and 1580 cm$^{-1}$ (conj C=C); nmr ($CDCl_3$) δ6.8–7.6 (m,1, —C$\underline{H}$=$CH_2$), 5.4–6.0 (m, 2, —CH=$C\underline{H}_2$), and 1.0 (t, 3, —$CH_2$—$C\underline{H}_3$).

2-Ethyl-3-formyl-2-cyclopentenone (5)

15.4 g (0.113 mole) of the vinyl compound 4 in 320 ml of THF was added to a 1-liter, round-bottom flask equipped with a 250 ml addition funnel and magnetic stirring bar. 4.4 ml of a solution prepared by solution of 0.783 g of osmium tetraoxide in 50 ml water was added dropwise. The mixture was stirred for 20 minutes and then a solution of 50.7 g (0.237 mole) sodium periodate in 396 ml of water was added over a 40-minute period. After completion of the addition the mixture was stirred for one hour and then filtered through a sintered glass funnel, using $CHCl_3$ to wash the precipitate. The filtrate was extracted with $CHCl_3$ and the combined chloroform extracts dried over anhydrous sodium sulfate ($NaSO_4$). The $CHCl_3$ was removed under reduced pressure to yield 15.0 g (0.109 mole, 96.2%) of a dark green crude liquid (aldehyde 5); uv max (95% ethanol) 247 and 256 nm; ir (neat) 1710 and 1670 cm$^{-1}$ (C=O); nmr ($CDCl_3$) δ9.7 (s, 1, C—H) and 1.2 (t, 3, —$CH_2$—$C\underline{H}_3$).

3-(Trans-3-keto-1-pentenyl)-2-ethyl-2-cyclopentenone (Ia)

5.0 g (0.104 mole) of a 50% NaH dispersion was transferred into a dry 1-liter, 3-neck flask equipped with an addition funnel, overhead stirrer and septum, and covered with 500 ml of dimethoxyethane (DME), and a solution of 23.4 g (0.130 mole) of dimethyl (2-oxobutyl) phosphonate in 30 ml DME was added dropwise over a 10-minute period. The mixture is stirred for 1 hour at room temperature to form the sodium salt of the phosphonate. A solution of 17.9 g (0.130 mole) of crude aldehyde 5 in 60 ml of DME was added dropwise over a 15-minute period, and the mixture stirred an additional 2 hours. The reaction was terminated by addition of 7.7 ml of glacial acetic acid followed by 200 ml of water. The reaction mixture was extracted with chloroform, and the chloroform extracts washed with water and dried over sodium sulfate. The chloroform was removed under reduced pressure to yield 30.5 g of a yellow product. This material, chromatographed over silicic acid using ethyl acetate-cyclohexane as the solvent system, yielded 18.5 g (75%) of a light yellow liquid, precursor Ia: uv max (95% ethanol) 293 nm; ir (neat)=1685, 1665, 1640 and 1580 cm$^{-1}$ (conjugated O=C—C=C—C=C—C=O); nmr (CDCl$_3$)

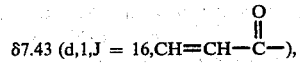

δ7.43 (d,1,J = 16,CH=CH—C—),

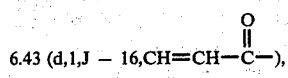

6.43 (d,1,J — 16,CH=CH—C—), 1.07 (t,3, —CH$_2$—CH$_3$), and 1.09 (t,3,CH$_2$CH$_3$).

PRECURSOR Ib 3-(Trans-3-keto-1-butenyl)-2-ethyl-2-cyclopentenone (Ib)

0.968 (0.023 mole) of a 57% NaH dispersion was transferred into a dry 250 ml flask equipped with a magnetic stirring bar and nitrogen inlet. The NaH was covered with 60 ml of dry DME and a solution of 4.15 g (0.025 mole) of dimethyl (2-oxopropyl) phosphonate in 10 ml of DME was added dropwise. The resulting reaction mixture was stirred for one hour at room temperature. Crude aldehyde 5 supra [from oxidation of 3.4 g (0.025 mole) of the vinyl compound 4] in 15 ml of DME was added dropwise, and the stirring was continued for 2 hours after completion of the addition. The reaction mixture was neutralized with acetic acid and 150 ml of water added. The resulting solution was extracted four times each with 100 ml of ether, and the combined ether extracts back-extracted with 100 ml water and once with 75 ml saturated NaCl. The extracts were dried over MgSO$_4$ and concentrated to yield 3.3 g of crude dione Ib. This material was chromatographed on silicic acid using ethyl acetate-cyclohexane to give a bright yellow liquid: uv (95% ethanol) 293 nm; ir (neat) 1685, 1665, 1640 and 1580 cm$^{-1}$ (conjugated enone system);

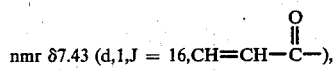

nmr δ7.43 (d,1,J = 16,CH=CH—C—),

6.43 (d,1,J = 16,CH=CH—C—), 2.3 (s,3,C—CH$_3$)

and 1.0 (t,3,CH$_2$CH$_3$).

PRECURSOR Ic 3-(Trans-3-keto-1-octenyl)-2-ethyl-2-cyclopentenone (Ic)

1.7 g (0.035 mole) of a 50% NaH dispersion is transferred into a dry 500 ml 3-neck flask equipped with an addition funnel, overhead stirrer and septum. The NaH was covered with 175 ml of DME and a solution of 10.1 g (0.045 mole) dimethyl (2-oxoheptyl) phosphonate in 12 ml of DME is added dropwise over a 10 minute period. The mixture is stirred for 1 hour at room temperature to form the sodium salt of the phosphonate. A solution of the crude aldehyde 5 supra [from oxidation of 7.0 g (0.05 mole) of the vinyl compound 4] in 25 ml of DME was added over a twenty-minute period, and the mixture was stirred an additional two hours. The reaction was terminated by the addition of 2.5 ml glacial acetic acid followed by 175 ml water. The reaction mixture was extracted with CHCl$_3$, and the combined organic extracts washed with water and dried over sodium sulfate. The CHCl$_3$ was removed under reduced pressure to yield 12.6 g of crude product. This material was chromatographed over silicic acid using ethyl acetate-cyclohexane for elution to give 6.7 g (80%) of a yellow liquid Ic. The spectral characteristics of this compound were similar to Ia and Ib with the

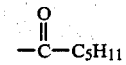

group evident in the nmr spectrum, —(CH$_2$)$_4$CH$_3$ at δ0.9.

PRECURSOR IIb

3-Methoxy-2-methyl-2-cyclopentenone (7)

20 g of commercially available 2-methyl-1,3-cyclopentanedione 2 in THF, was treated with diazomethane generated from 50 g of N-methyl-N-nitroso-p-toluenesulfonamide, sold under the trademark Diazald (Aldrich Chemical Company). After standing at room temperature for two hours, the solvent was removed under reduced pressure to give ca. 20 g of crude enol ether. The crude product from several reactions was combined and extracted with 5% NaHCO$_3$. After removal of the solvent, the product 7 obtained was free of unreacted starting material 6 as determined by nmr analysis. Distillation of this material gave a white, low-melting solid: nmr (CDCl$_3$) δ4.0 (s,3, —OCH$_3$).

3-Vinyl-2-methyl-2-cyclopentenone (8)

A one-liter, three-necked flask equipped with a mechanical stirrer, reflux condenser, dropping funnel and nitrogen inlet was flamed out under nitrogen. After 65.6 g (0.05 mole) vinyl magnesium bromide in 500 ml THF was transferred to the reaction flask, 23.3 g (0.18 mole) of 3-methoxy-2-methyl-2-cyclopentenone 7 in 100 ml of dry THF was then added dropwise over a period of several hours. For the reasons supra, methanol with p-toluenesulfonic acid, may be preferred for larger quantity production. The mixture was cooled and then stirred into a four-liter beaker containing 1 kg of cracked ice. After adjustment to pH 3 with concentrated HCl, the reaction mixture was extracted with CHCl$_3$. After washing the combined chloroform extracts with water, the solvent was removed under reduced pressure to give 19.7 g of a yellow liquid. This material was distilled (55°–56° C. at 0.1 mm) to give a 60% yield:nmr (CDCl$_3$) δ7.2–5.2 (m,3, —CH=CH$_2$) and 1.8 (s,3, —CH$_3$).

2-Methyl-3-formyl-2-cyclopentenone (9)

3.0 g (0.025 mole) of the vinyl compound 8 in 90 ml of THF was added to a 500-ml, round-bottom flask equipped with a 250 ml addition funnel and magnetic stirring bar. 0.96 ml of a solution prepare by dissolution of 0.783 g of osmium tetroxide in 50 ml of water was added dropwise. The mixture was stirred for 20 minutes then a solution of 11.2 g of sodium periodate in 88 ml of water was added over a 40 minute period. After completion of the addition, the mixture was stirred for one hour and then filtered through a sintered glass funnel, using CHCl$_3$ to wash the precipitate. The filtrate was extracted with chloroform and the combined extracts were dried over sodium sulfate. The chloroform was removed under reduced pressure to give 2.8 g of a dark green liquid 9: nmr (CDCl₃) δ10.3 (s, 1, —C$\underline{H}$=O) with the disappearance of the vinyl absorption of compound 8.

3-(Trans-3-keto-1-butenyl)-2-methyl-2-cyclopentenone (IIb)

In a dry 500-ml flask equipped with a magnetic stirring bar and nitrogen inlet was added 0.77 g (0.016 mole) of a 50% NaH dispersion. The NaH dispersion was covered with 100 ml of DME and a solution of 3.32 g (0.020 mole) of dimethyl (2-oxopropyl)phosphonate in 10 ml DME was added dropwise over a 10 minute period and then the mixture was stirred an additional hour at room temperature to form the sodium salt of the phosphonate. A solution of 2.5 g (0.020 mole) of the aldehyde 9 in 10 ml DME was added over a 15 minute period and then the mixture was stirred an additional two hours. The reaction was terminated by the addition of 1 ml of glacial acetic acid followed by 150 ml of water. The reaction mixture was extracted with CHCl₃, the combined organic extracts washed with water and dried over sodium sulfate. The chloroform was removed under reduced pressure to give 3.4 g of a yellow liquid. This material was chromatographed over silicic acid using ethyl acetate-cyclohexane to give 1.3 g of a yellow liquid IIb: uv max (95% ethanol) 290 nm; ir (neat) 1685, 1665, 1640 and 1580 cm⁻¹ (conjugated enone system); nmr δ7.76

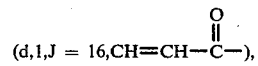

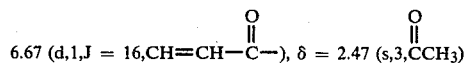

and 1.97 (t,3,J very small, C—C$\underline{H}_3$).

The preparation of precursors IIa and IIc, but for the different reactants indicated in Table I supra, follow very closely those of the foregoing examples.

When precursor Ia was treated with ethanolic hydroxide under conditions used for the conversion of 15-keto-PGB₁ methyl ester to PGB$_x$, U.S. Pat. No. 4,245,111 supra, the reaction proceeded in a manner similar to that of 15-keto-PGB₁ to give an oligomerized product exhibiting the general spectral characteristics of PGB$_x$. When the precursor Ia was oligomerized and worked up in a manner analogous to that of PGB$_x$, the crude oligomers exhibited biological activities, although less than that of PGB$_x$ at a similar stage of purification, in the protection of oxidative phosphorylation in aged degenerated mitochondria. Fractionation of the crude product by chromatography gave fractions of varying degrees of biological activity in the protection of oxidative phosphorylation in degraded mitochondria.

These observations are significant for several reasons. An active material can be derived from precursor Ia which provides the first evidence suggesting that the carboxylic acid functionality of the prostaglandins may not be essential for biological activity. Since the ethyl analog and related compounds possess the same conjugated cyclopentenone functionality as 15-keto-PGB₁, it is expected that the oligomerization should take place chemically in the same manner at 15-keto-PGB₁. Because of the lower molecular weight of the precursors Ia, b, c and IIa, b, c relative to 15-keto-PGB₁ due to the abbreviated side chains, the oligomers produced therefrom are more amenable to structural elucidation by conventional spectroscopic approaches. For example, the precursor Ia gives an oligomer having the same number of units as PGB$_x$, and the lower molecular weight of the oligomer should allow the direct molecular weight determination by mass spectrometry.

Precursors according to the present invention are more amenable to structural elucidation of the polymers derived therefrom since they allow a more definitive assignment of the carbon-13 chemical shifts associated with the cyclopentenone ring system. Previous chemical shift assignments for the structural elucidation of intermediates isolated from the formation of PGB$_x$ were based on analogy to other classes of prostaglandins not having the disubstituted cyclopentenone system, and thus several assignments associated with this system were uncertain.

The chemical shift assignments achieved with the present invention are summarized in Table 2 below. The numbering system for the compounds are as follows:

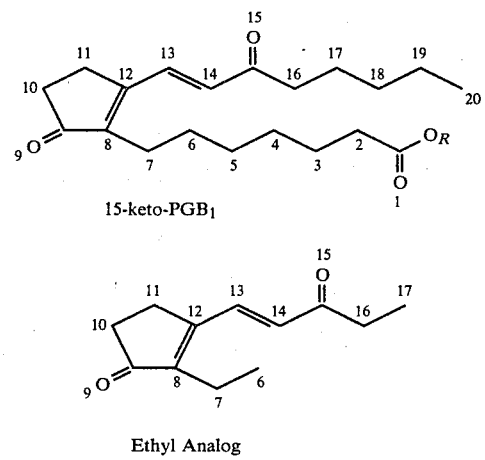

The nmr spectra were determined with a Varian CF-20 spectrometer with CDCl₃ as the solvent and TMS as the internal reference. The chemical shifts are given in ppm relative to TMS, and the multiplicities were determined in separate proton off-resonance decoupling experiments.

TABLE II

|  | 8 | 4 | Ib | Ia | Ic | 15-keto-PGB₁ |
|---|---|---|---|---|---|---|
| C(1) |  |  |  |  |  | s, 174.09 |
| C(2) |  |  |  |  |  | t, 33.97 |
| C(3) |  |  |  |  |  | t, 24.80 |
| C(4) |  |  |  |  |  | t, 29.23 |
| C(5) |  |  |  |  |  | t, 28.86 |
| C(6) |  | q, 13.47 | q, 13.67 | q, 13.65 | q, 13.67 | t, 28.86 |

TABLE II-continued

| | 8 | | 4 | | Ib | | Ia | | Ic | | 15-keto-PGB$_1$ | |
|---|---|---|---|---|---|---|---|---|---|---|---|---|
| C(7) | q, | 8.01 | t, | 16.28 | t, | 16.81 | t, | 16.78 | t, | 16.80 | t, | 23.41 |
| C(8) | s, | 137.26 | s, | 143.03 | s, | 149.23 | s, | 149.04 | s, | 149.10 | s, | 147.76 |
| C(9) | s, | 209.75 | s, | 209.35 | s, | 208.75 | s, | 208.69 | s, | 208.82 | s, | 208.84 |
| C(10) | t, | 33.56 | t, | 33.79 | t, | 33.92 | t, | 33.94 | t, | 33.95 | t, | 33.89 |
| C(11) | t, | 25.14 | t, | 24.99 | t, | 25.40 | t, | 25.42 | t, | 25.44 | t, | 25.45 |
| C(12) | s, | 163.42 | s, | 163.01 | s, | 159.56 | s, | 159.71 | s, | 159.79 | s, | 160.18 |
| C(13) | d, | 131.32 | d, | 131.13 | d, | 134.82 | d, | 133.85 | d, | 133.93 | d, | 134.01 |
| C(14) | t, | 120.92 | t, | 120.91 | d, | 131.35 | d, | 130.45 | d, | 130.69 | d, | 130.60 |
| C(15) | | | | | s, | 197.89 | s, | 200.40 | s, | 200.20 | s, | 200.16 |
| C(16) | | | | | q, | 28.13 | t, | 34.70 | t, | 41.50 | t, | 41.57 |
| C(17) | | | | | | | q, | 7.93 | t, | 23.79 | t, | 23.82 |
| C(18) | | | | | | | | | t, | 31.43 | t, | 31.43 |
| C(19) | | | | | | | | | t, | 22.50 | t, | 22.49 |
| C(20) | | | | | | | | | q, | 13.93 | q, | 13.91 |
| C(21) | | | | | | | | | | | s, | 51.41 |

Some of the many advantages of the present invention should now be apparent. For example, the prostaglandin analog 3-(trans-3-keto-1-pentenyl)-2-ethyl-2-cyclopentenone Ia and the related compounds afford a number of distinct advantages over prior art precursors such as the prostaglandin 15-keto-PGB$_1$ for oligomeric mixtures exhibiting the unique property of protection of the in vitro phosphorylation ability of degraded mitochondria. Compared to the prostaglandin 15-keto-PGB$_1$, for example, the analog 3-(trans-3-keto-1-pentenyl)-2-ethyl-2-cyclopentenone is readily available from a much more efficient synthetic route. Oligomeric mixtures derived from these analogs do no exhibit inhibitions of oxidative phosphorylation at higher oligomer concentrations as does oligomeric mixtures derived from 15-keto-PGB$_1$. In addition, due to the relative simplicity of the analog structures, according to the invention, oligomeric mixtures derived from these compounds are much more amenable to structure elucidation by spectroscopic techniques than oligomeric mixtures derived from the prostaglandin 15-keto-PGB$_1$.

It will be understood that various changes in the details, materials, and steps, which have been herein described and illustrated in order to explain the nature of the invention, may be made by those skilled in the art within the principle and scope of the invention as expressed in the appended claims.

What is claimed is:

1. A prostaglandin analog for oligomerization to mixtures exhibiting protection of oxidative phosphorylation of degenerated mitochondria of the formula:

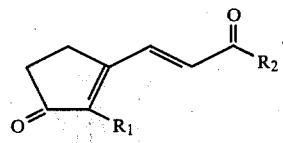

wherein R$_1$ and R$_2$ are alkyls.

2. A prostaglandin analog according to claim 1 wherein R$_1$ is ethyl or methyl, and R$_2$ is ethyl, methyl or n-pentyl.

3. A process for preparation of prostaglandin analogs, comprising the steps of:
O-alkylating a 2-alkylcyclopentane-1,3-dione to form an enol ether;
reacting the enol ether with an effective amount of vinyl magnesium bromide in ether to form a vinyl compound;
oxidizing the vinyl compound with effective amounts of osmium tetraoxide and sodium periodate in aqueous ether to form an aldehyde; and
reacting the aldehyde with an effective amount of a dimethyl (2-oxoalkyl)phosphonate to form a crude product containing the precursor.

4. A process according to claim 3 wherein said dione is 2-ethyl-1,3-cyclopentanedione or 2-methyl-1,3-cyclopentanedione.

5. A process according to claim 4 wherein said phosphonate is dimethyl (2-oxobutyl)phosphonate, dimethyl (2-oxopropyl)phosphonate, or dimethyl (2-oxoheptyl)phosphonate.

6. A process for preparation of prostaglandin analogs, comprising the steps of:
O-alkylating a 2-alkylcyclopentane-1,3-dione to form an enol ether;
reacting 1 part of said enol ether with 1.87 to 2.81 parts of vinyl magnesium bromide in ether to form a vinyl compound;
oxidizing the vinyl compound with 0.004 to 0.015 part osmium tetraoxide and 3.292 to 3.73 parts sodium periodate in aqueous ether to form an aldehyde; and
reacting said aldehyde in DME with an effective amount of a dimethyl (2-oxoalkyl)phosphonate to form a crude product containing the precursor.

7. A process for preparation of a precursor comprising the steps of:
O-alkylating 2-ethyl-1,3-cyclopentanedione partially dissolved in aqueous ether with an effective amount of etheral diazomethane to form an enol ether;
reacting 1 part of said enol ether in ether with 1.87 parts vinyl magnesium bromide in ether to form a vinyl compound;
oxidizing 1 part of said vinyl compound in an aqueous ether solution of 0.004 part osmium tetraoxide and 3.292 parts sodium periodate to form an aldehyde; and
reacting 1 part of said aldehyde in DME with 1.31 parts dimethyl (2-oxobutyl)phosphonate and 0.28 part NaH dispersion.

8. A process for preparation of a precursor comprising the steps of:
O-alkylating 2-ethyl-1,3-cyclopentanedione partially dissolved in aqueous ether with an effective amount of etheral diazomethane to form an enol ether;

reacting 1 part of said enol ether in ether with 1.87 parts vinyl magnesium bromide in ether to form a vinyl compound;

oxidizing 1 part of said vinyl compound in an aqueous ether solution of 0.004 part osmium tetraoxide and 3.292 parts sodium periodate to form an aldehyde; and reacting said aldehyde oxidized from 1 part of said vinyl compound in DME with 1.22 parts dimethoxy-2(oxopropyl) phosphonate and 0.28 part NaH dispersion.

9. A process for preparation of a precursor comprising the steps of:

O-alkalylating 2-ethyl-1,3-cyclopentanedione partially dissolved in aqueous ether with an effective amount of etheral diazomethane to form an enol ether;

reacting 1 part of said enol ether in ether with 1.87 parts vinyl magnesium bromide in ether to form a vinyl compound;

oxidizing 1 part of said vinyl compound in an aqueous ether solution of 0.004 part osmium tetraoxide and 3.292 parts sodium periodate to form an aldehyde; and reacting said aldehyde oxidized from 1 part of said vinyl compound in DME with 1.44 parts dimethyl-(2-oxoheptyl) phosphonate and 0.24 part NaH dispersion.

10. A process for preparation of a precursor comprising the steps of:

treating a solution of 2-methyl-1,3-cyclopentanedione in THF with an effective amount of etheral diazomethane to form an enol ether;

reacting 1 part of said enol ether in ether with 2.81 part vinyl magnesium bromide to form a vinyl compound;

oxidizing 1 part of said vinyl compound in an aqueous ether solution of 0.015 part osmium tetraoxide and 3.73 parts sodium periodate to form an aldehyde; and reacting 1 part of said aldehyde in DME with 8.3 parts dimethyl-(2-oxoprophyl)phosphonate and 0.308 part NaH dispersion.

* * * * *